United States Patent [19]

Wörder

[11] 4,361,149
[45] Nov. 30, 1982

[54] INJECTION SYRINGE

[75] Inventor: Hans Wörder, Bünde, Fed. Rep. of Germany

[73] Assignee: Bünder Glas GmbH, Bünde, Fed. Rep. of Germany

[21] Appl. No.: 256,514

[22] Filed: Apr. 22, 1981

Related U.S. Application Data

[63] Continuation of Ser. No. 133,661, Mar. 25, 1980, abandoned, which is a continuation of Ser. No. 934,651, Aug. 17, 1978, abandoned.

[30] Foreign Application Priority Data

Aug. 27, 1977 [DE] Fed. Rep. of Germany ....... 2738676

[51] Int. Cl.³ .............................................. A61M 5/00
[52] U.S. Cl. .............................. 128/215; 128/218 DA
[58] Field of Search ................... 128/215, 216, 218 R, 128/218 DA, 218 NV, 218 N, 218 D, 220, 221, 272.3

[56] References Cited

U.S. PATENT DOCUMENTS

| | | | |
|---|---|---|---|
| 2,512,568 | 6/1950 | Saffir | 128/215 |
| 3,314,429 | 4/1967 | Boehm et al. | 128/232 |
| 3,811,441 | 5/1974 | Sarnoff | 128/218 DA |
| 3,989,044 | 11/1976 | Meierhoefer | 128/218 N |
| 4,048,588 | 4/1978 | Koenig | 128/218 DA X |
| 4,059,112 | 11/1977 | Tischlinger | 128/272.3 |

Primary Examiner—John D. Yasko
Attorney, Agent, or Firm—Murray and Whisenhunt

[57] ABSTRACT

The invention provides an injection syringe of the kind comprising one or two sterile units, which has a full cylinder ampoule the rear end of which is sealed by a plug serving as a piston, and the front end of which is sealed by a pierceable seal, and with a unit in form of a syringe body formed as a support with or without a tubular needle, for the accommodation of a cylinder ampoule and a tubular needle shield, characterized by the syringe body for accommodating the full cylinder ampoule being developed as a plastic body and, in the inside space being provided with a bored-through piercing point projecting inwards, the bored-through piercing point also consisting of plastic and forming one unit with the syringe body.

5 Claims, 2 Drawing Figures

INJECTION SYRINGE

This is a continuation application of Ser. No. 133,661, filed Mar. 25, 1980, now abandoned which is a continuation of Ser. No. 934,651, filed Aug. 17, 1978, now abandoned.

This invention relates to an injection syringe comprising one or two sterile units, which has a full cylinder ampoule the rear end of which is sealed by a plug serving as a piston, and the front end of which is sealed by a piercable seal, and with a unit in the form of a syringe body as a support, with or without tubular needle, for the accommodation of a cylinder ampoule and a needle shield.

THE PRIOR ART

Injection syringes are commonly known in human medicine. Injection syringes of this type are used for the application of dissolved medicines, whereby the injection may be carried out subcutaneously, intramuscularly, intravenously or in any other known way.

In this context injection syringes are known which are either provided with a fitted sterile injection needle or in which—in each individual case—separately packed sterile injection needles are inserted or are still interchangeable. In addition, disposable injection syringes are known, which offer the same possibilities.

Normally, these injection syringes consist of a combination of glass and plastic parts in combination with rubber for sealing the glass cylinders, and a needle combination for the application. The main functioning parts are the syringe body for holding the medicine in liquid or dry form and the piston operable from the outside by means of a piston rod, which directs the medicine through the discharge opening in the neck of the syringe body via a tubular needle or a cone with attached tubular needle into the human body.

It is generally known that disposable syringes are fitted with needles or needle-like parts which upon piercing through a diaphragm make the connection with the solution and, depending on whether they are developed as a cone or as an injection needle at the upper end, offer the possibility for applying the product. However, the parts concerned are generally fitted and largely consist of special steel.

OBJECT OF THE INVENTION

The inventor set himself the task of disclosing an improvement in this field which on the one hand offers the possibility of advanced handling and which, on the other hand, is reasonable in price.

SUMMARY OF THE INVENTION

According to the invention we provide an injection syringe of the kind having a body formed with a chamber for receiving a cylindrical ampoule of the kind having a sealing plug at one end serving as a piston and a piercible seal at the other end, the provision of a piercing point extending axially within the body in the chamber capable of entry into said ampoule when the latter is pressed axially into said chamber, said piercing point having a bore therethrough to effect communication of the interior of said ampoule with the exterior of the syringe body when the piercing point has penetrated the seal, and said piercing point being formed integrally with said syringe body as a one-piece plastic unit.

The angle of the piercing point varies depending on the range of application, i.e. between 30° and 75° and may extend outwards from inside in a funnel-shaped manner. If required, it is also possible to have the front end of the bored-through piercing point designed flat. Beyond this, the opposite side of the syringe body, i.e. the outer part of same, is developed in form of a Luer or Record cone or similar.

The actual design of the syringe body for the cylinder ampoule is of no inportance in this case. It may be of the design shown in the drawing, or of any other design.

With this type of production, it is obvious that both the inside piercing point as well as the outer cone are always manufactured of the same material as the plastic syringe body.

The inner piercing point is arranged in such a way that it pierces rubber diaphragms of a certain thickness and Shore hardness without any trouble and guarantee adequate sealing with the compression stress between plastic and rubber during the application.

BRIEF DESCRIPTION OF THE DRAWINGS

One exemplified embodiment of the subject of the invention in the form of an injection syringe is shown in the drawings, with the subsequent description serving as an explanation of the subject of the invention.

In the drawings.

DESCRIPTION OF THE PREFERRED EMBODIMENT

Figure 1:
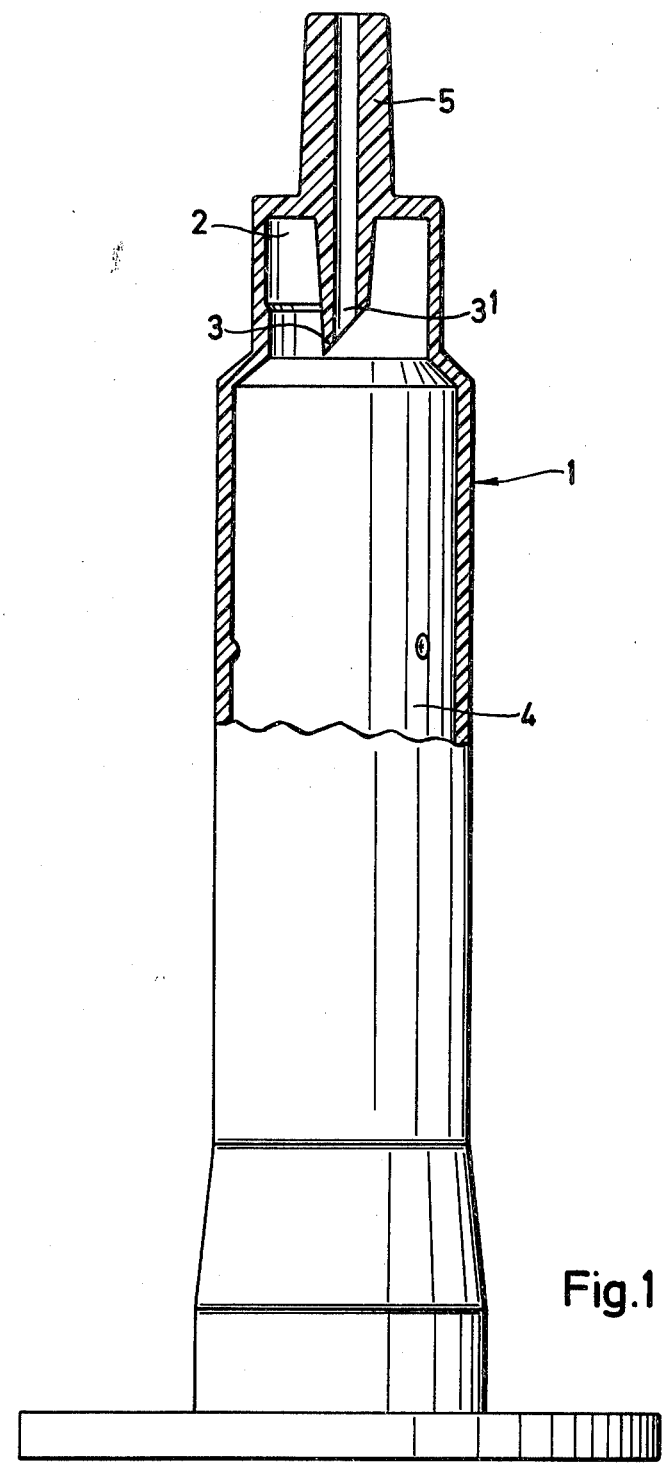
FIG. 1 represents an elevation of an injection syringe, and a part-sectional view.
Figure 2:
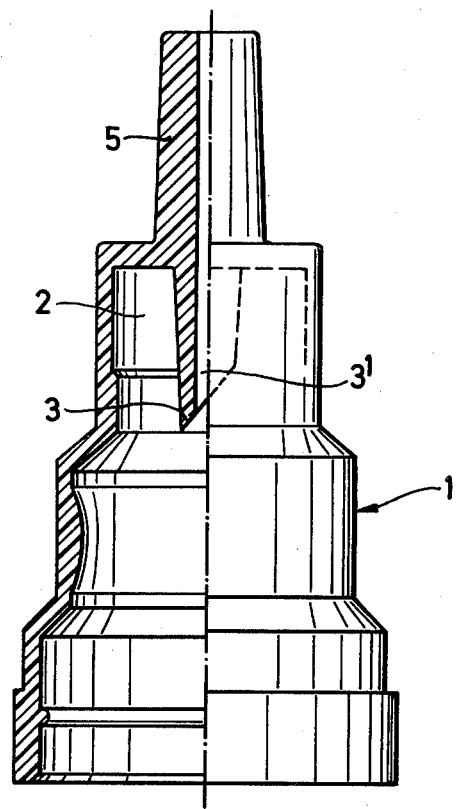
FIG. 2 represents the syringe body of the invention as a part-sectional view and an elevation according to FIG. 1.

In FIGS. 1 and 2, the syringe body of the invention has been denoted by 1. The syringe body 1 consists of a thin-walled plastic and is of a step-like design having a chamber 4. A piercing point 3 projects in the inside space 2 of the syringe body 1, this piercing point 3 being provided with a bore $3^1$. This piercing point 3 pierces through the rubber diaphragm of the cylinder ampoule within the chamber 4 without difficulty. In this instance, the angle of the bored-through piercing point 3 is 45° and extends outwards from inside in a funnel-shaped manner.

The opposite side of the syringe body 1, i.e. the outer part of same, is developed in the present instance in form of a cone 5 with increased wall thickness.

The present exemplified embodiment only serves as a possible representation, and it is pointed out explicitly that other exterior designs of the syringe frame are possible without them falling outside the range of protection as defined by the appended claims.

I claim:

1. In an injection syringe of the kind having a body formed with a chamber for receiving by axial movement a cylindrical ampoule of the kind having a sealing plug at one end serving as a piston and a piercable seal at the other end, the provision of (a) a piercing point extending axially within the body into the chamber capable of entry into said ampoule by penetrating said seal when the ampoule is pressed axially into said chamber, (b) said piercing point having a bore therethrough to effect communication of the interior of said ampoule with the exterior of the syringe body when the piercing point has penetrated the seal, (c) the outer surface of said piercing point being inwardly tapered over the entire length thereof, whereby the compression stress between the tapered piercing point and pierced seal ensures sealing therein between,
(d) said piercing point being formed integrally with said syringe body as a one-piece plastic unit, and
(e) a conical shaped projection integral with said body for reception of a needle assembly, said projection having therein a continuation of the bore within said piercing point.

2. An injection syringe according to claim 1, wherein the piercing point is formed with an oblique surface having an angle of between 30° and 75° to the body axis.

3. An injection syringe according to claim 1, wherein the piercing point has a frusto conical exterior surface.

4. An injection syringe according to claim 1, wherein the lower end of the piercing point is flat.

5. An injection syringe according to claim 1, wherein said body is formed with a conical shaped projection integral with said body for reception of a needle assembly, said projection having therein a continuation of the bore within said piercing point.

* * * * *